United States Patent
Miyata et al.

(10) Patent No.: US 6,297,193 B1
(45) Date of Patent: Oct. 2, 2001

(54) ALGAL GROWTH OR MICROBIAL PROLIFERATION INHIBITORS AND USE THEREOF

(75) Inventors: Shigeo Miyata, Kitakyushu; Hitoshi Manabe, Takamatsu; Teruko Shimada, Sakaide, all of (JP)

(73) Assignees: Kyowa Chemical Industry Co., Ltd., Kagawa-ken; Kabushikikaisha Kaisui Kagaku Kenkyujo, Fukuoka-ken, both of (JP)

(*) Notice: Subject to any disclaimer, the term of this patent is extended or adjusted under 35 U.S.C. 154(b) by 0 days.

(21) Appl. No.: 09/367,601

(22) PCT Filed: Dec. 18, 1998

(86) PCT No.: PCT/JP98/05735

§ 371 Date: Aug. 18, 1999

§ 102(e) Date: Aug. 18, 1999

(87) PCT Pub. No.: WO99/30564

PCT Pub. Date: Jun. 24, 1999

(30) Foreign Application Priority Data

Dec. 18, 1997 (JP) .................................................. 9-364650

(51) Int. Cl.$^7$ .......................... A01N 59/06; A01N 59/16; A01N 59/20
(52) U.S. Cl. .............................................................. 504/152
(58) Field of Search .............................................. 504/152

(56) References Cited

U.S. PATENT DOCUMENTS 5,741,526 * 4/1998 Miyata .................................. 424/635

FOREIGN PATENT DOCUMENTS

| 8-48606 | * 2/1966 | (JP) . |
| 52-110734 | 9/1977 | (JP) . |
| 6-65011 | 3/1994 | (JP) . |
| 6-72816 | 3/1994 | (JP) . |
| 8-291011 | 11/1996 | (JP) . |

* cited by examiner

Primary Examiner—S. Mark Clardy
(74) Attorney, Agent, or Firm—Wenderoth, Lind & Ponack, L.L.P.

(57) ABSTRACT

An antialgal method, which employs, as an antialgal component, at least one solid solution selected from the group consisting of specific hydroxide or oxide solid solutions and an organic or inorganic material containing the antialgal component.

4 Claims, No Drawings

ALGAL GROWTH OR MICROBIAL PROLIFERATION INHIBITORS AND USE THEREOF

This is a 371 of PCT/JP98/05735, filed Dec. 18, 1998.

1. Technical Field of the Invention

The present invention relates to an inhibitor against the growth of algae or against the proliferation of microorganisms in water-use facilities and use thereof. More specifically, it relates to a inhibitor which inhibits the growth of algae or the proliferation of microorganisms such as water bloom and red tide in water treatment facilities for utilizing river water or rain water as drinking water or daily life water by means of clarification, pipes for water supply or waste water, tanks for breeding or transporting fish and shellfish, a swimming pool, a solar bath tank, water which ponds during excavation, lakes, rivers, dams and the sea, and use thereof.

2. Technical Background

Algae grow by undergoing photosynthesis. In this respect, algae are different from bacteria or fungi. When algae appear, fungi which propagate with algae increase and water is therefore polluted and putrefied in water-use facilities. Further, the growth of algae clogs a pipe or a machine. While shading can inhibit the growth of algae, it is difficult in practical use. There has been so far employed a method of adding an agent such as chlorine or sodium hypochlorite as a method for preventing the growth of algae. However, chlorine reacts with a humin in soil, and forms trihalomethane which is a harmful organic halide.

In a water area which has a small coming and going of water, such as lake, pond or bog, alimentation is likely to increase due to the deposition of organic materials. The increase of alimentation causes a generation of biological plankton such as red tide or water bloom and a generation of a methane gas, whereby the state where the amount of dissolved oxygen is extremely small occurs. When red tide or water bloom occurs, it is waited that the red tide or water bloom naturally disappears or the red tide or water bloom is pumped up together with water by means of a large pump ship and treated in an overland waste-water-treatment plant. However, the above recover of the red tide or water bloom with a pump ship requires a great deal of labor, time and cost, and it lacks efficiency. When waited for the natural disappearance, a great deal of oxygen in water is spent at a decomposing time. This causes the death of culture fishes in volume or the generation of bad smell.

The present inventors have made diligent studies for overcoming the above problems and as a result succeeded in providing an inhibitor to prevent the growth of algae or the proliferation of microorganisms, which inhibitor per se is nonpoisonous or has an extremely low toxicity, which inhibitor is excellent in heat resistance and weather resistance, which inhibitor is inexpensive, and which inhibitor has excellent effects of preventing the growth of algae as compared with chlorine and sodium hypochlorite, and an organic or inorganic material, such as resin, a rubber composition, a hydraulic cement composition and a coating composition, containing the above inhibitor.

Disclosure of the Invention

The present invention provides an algal growth or microbial proliferation inhibitor, which is characterized by containing, as an active component, at least one solid solution selected from the group consisting of the compounds of the following formulae (1) to (4), the compounds of the following formulae (1) to (4) being a hydroxide solid solution of the formula (1), $$[(M_1^{2+})_y(M_2^{2+})_{1-y}]_{1-x}M^{3+}_x(OH)_2(A^{n-})_{y/n} \cdot mH_2O \qquad (1)$$

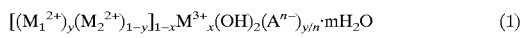

wherein y is a number in the range of $0 \leq y \leq 1$, preferably $0 < y \leq 1$, x is a number in the range of $0 < x \leq 0.5$, preferably $0.01 \leq x \leq 0.5$, m is a number in the range of $0 \leq m \leq 2$, $M_1^{2+}$ is $Zn^{2+}$ and/or $Cu^{2+}$, $M_2^{2+}$ is $Mg^{2+}$ and/or $Ca^{2+}$, $M^{3+}$ is at least one trivalent metal, and $A^{n-}$ is an anion of n valence, an oxide solid solution of the formula (2), $$[(M_1^{2+})_y(M_2^{2+})_{1-y}]_{1-x}M^{3+}_{x-a}O \qquad (2)$$

wherein y is a number in the range of $0 \leq y \leq 1$, preferably $0 < y \leq 1$, x is a number in the range of $0 < x \leq 0.5$, preferably $0.01 \leq x \leq 0.5$, x–a means that the number of $M^{3+}$ is decreased by a due to a lattice defect, and $M_1^{2+}$ and $M_2^{2+}$ have the same meanings as those defined in the formula (1), a hydroxide solid solution of the formula (3), $$(M_1^{2+})_x(M_2^{2+})_{1-x}(OH)_2 \qquad (3)$$

wherein x is a number in the range of $0.0001 \leq x < 0.9$, and $M_1^{2+}$ and $M_2^{2+}$ have the same meanings as those defined in the formula (1), and an oxide solid solution of the formula (4), $$(M_1^{2+})_x(M_2^{2+})_{1-x}O \qquad (4)$$

wherein x is a number of in the range of $0.0001 \leq x < 0.9$, and $M_1^{2+}$ and $M_2^{2+}$ have the same meanings as those defined in the formula (1).

Further, the present invention provides an organic or inorganic material which is characterized in that 100 parts of the organic or inorganic material contains 0.001 to 50 parts by weight, preferably 0.001 to 15 parts by weight, more preferably 0.01 to 5 parts by weight, of the above algal growth or microbial proliferation inhibitor.

Most Preferred Embodiment of the Invention

The inhibitor of the present invention is remarkably excellent in effects of preventing the growth of algae, or the like, as compared with chlorine or sodium hypochlorite, and has very low toxicity on living things. Since, further, the inhibitor of the present invention is excellent in heat resistance, the inhibitor of the present invention does not cause bubbles at a molding temperature of a resin or a rubber and there can be easily and effectively produced an organic or inorganic material containing the above inhibitor.

The hydroxide solid solution, i.e., hydrotalcite compound, of the formula (1), $$[(M_1^{2+})_y(M_2^{2+})_{1-y}]_{1-x}M^{3+}_x(OH)_2(A^{n-})_{y/n} \cdot mH_2O \qquad (1)$$

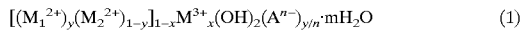

wherein y is a number in the range of $0 \leq y \leq 1$, x is a number in the range of $0 < x \leq 0.5$, m is a number in the range of $0 \leq m \leq 2$, $M_1^{2+}$ is $Zn^{2+}$ and/or $Cu^{2+}$, $M_2^{2+}$ is $Mg^{2+}$ and/or $Ca^2$, $M^{3+}$ is at least one trivalent metal, and $A^{n-}$ is an anion of n valence, can be easily produced by any one of conventionally known methods. For example, the production process thereof is described in detail in JP-B-46-2280, JP-B-47-32198, JP-B50-30039, JP-B-56-29893, etc.

The oxide solid solution of the formula (2),

$$[(M_1^{2+})_y(M_2^{2+})_{1-y}]_{1-x}M^{3+}_{x-a}O \qquad (2)$$

wherein y is a number in the range of $0 \leq y \leq 1$, x is a number in the range of $0 < x \leq 0.5$, x−a means that the number of $M^{3+}$ is decreased by a due to a lattice defect, and $M_1^{2+}$ and $M_2^{2+}$ have the same meanings as those defined in the formula (1), can be produced by calcining the hydrotalcite compound of the formula (1) at about 300° C. to 900° C., preferably about 400° C. to 700° C., for about 0.1 to 10 hours.

The hydroxide solid solution of the formula (3),

$$(M_1^{2+})_x(M_2^{2+})_{1-x}(OH)_2 \qquad (3)$$

wherein x is a number of $0.0001 \leq x < 0.9$, and $M_1^{2+}$ and $M_2^{2+}$ have the same meanings as those defined in the formula (1), can be easily produced according to the method disclosed in JP-A-7-286101. The compound of the formula (3) is a solid solution in which $Cu^{2+}$ and/or $Zn^{2+}$ is/are dissolved in $Ca(OH)_2$ or $M_g(OH)_2$ and which has the same crystal structure as that of $Ca(OH)_2$ or $M_g(OH)_2$, and the compound of the formula (3) gives almost the same diffraction pattern as that of $Ca(OH)_2$ or $M_g(OH)_2$ by a powder X-ray diffraction. When "x" is larger than 0.9 in the formula (3), the solid solution of the formula (3) can not be formed and no effects of preventing the growth of algae and no effects of microorganism resistance can be exhibited.

When x is too small, the ejection concentration of copper ions and/or zinc ions as an active component is decreased, which makes the effects of the present invention insufficient. The higher the concentration of copper ions and/or zinc ions in the compoundof the formula (3) is, the lower the ejectability of copper ions and/or zinc ions to water is. Thus, the effect of preventing the growth of algae tends to be insufficient. Therefore, the range of "x" of the anti-alga and anti-microorganism agent of the present invention is $0.0001 \leq x \leq 0.9$, preferably $0.0001 \leq x < 0.4$, more preferably $0.0001 \leq x \leq 0.2$.

The oxide solid solution of the formula (4),

$$(M_1^{2+})_{1-x}(M_2^{2+})_xO \qquad (4)$$

wherein x is a number in the range of $0.0001 \leq x < 0.5$, and $M_1^{2+}$ and $M_2^{2+}$ have the same meanings as those defined in the formula (1), can be produced by calcining the hydroxide solid solution of the formula (3) at about 300° C. to 1,200° C., preferably about 400° C. to 900° C., for about 0.1 to 10 hours and then properly carrying out common procedures such as pulverization, surface-treatment, classification, etc., as required.

When the inhibitor of the present invention is incorporated into a resin or a rubber, for improving the dispersibility it is preferred to surface-treat the compounds of the formulae (1) to (4) with a common surface-treating agent such as higher fatty acid, alkaline metal salt or alkaline-earth metal salt of higher fatty acid, phosphates, a silane-containing coupling agent, a titanate-containing coupling agent, an aluminum-containing coupling agent, and esters of a polyalcohol and a fatty acid. More specifically the preferred surface-treating agent includes higher fatty acids having at least 10 carbon atoms such as stearic acid, erucic acid, palmitic acid, lauric acid, behenic acid; alkaline metal salts of the above higher fatty acids; sulfates of higher alcohols such as stearyl alcohol and oleyl alcohol; anion surfactants such as sulfate of polyethylene glycol ether, amide-bonded sulfate, ester-bonded sulfate, ester-bonded sulfonate, amide-bonded sulfonate, ether-bonded sulfonate, ether-bonded alkylallyl sulfonate, ester-bonded alkylallyl sulfonate and amide-bonded alkylallyl sulfonate; phosphoric acid esters such as mono or di ester of orthophosphoric acid and an oleyl alcohol or a stearyl alcohol or a mixture of monoester and diester, an acid thereof, an alkali metal salt thereof and an amine salt thereof; silane-containing coupling agents such as vinylethoxysilane, vinyl-tris(2-methoxy-ethoxy) silane, gamma-methacryloxypropyltrimethoxysilane, gamma-aminopropyltrimethoxysilane, beta(3,4-epoxycyclohexyl)ethyltrimethoxysilane, gamma-glycidoxypropyltrimethoxysilane and gamma-mercaptopropyltrimethoxysilane; titanate-containing coupling agents such as isopropyltriisostearoyltitanate, isopropyltris(dioctylpyrophosphate)titanate, isopropyltri(N-aminoehtyl-aminoethyl)titanate and isopropyltridecylbenzensulfonyltitanate; aluminumcontaining coupling agents such as acetoalkoxyaluminumdiisopropylate; and esters of a polyalcohol and a fatty acid such as glycerine monostearate and glycerine monooleate.

The compounds of the formulae (1) to (4) can be surface-coated with a surface-treating agent by a known wet method or a known dry method. In the wet method, for example, a surface-treating agent in a liquid state or in a emulsion state is added to a slurry of the above compound, and it is sufficient to mechanically fully mix the resultant mixture at a temperature of up to about 100° C. In the dry method, while fully stirring a powder of the above compound with a mixing machine such as a Henschel mixer, a surface-treating agent in a liquid, emulsion or solid state is added, and it is sufficient that the resultant mixture is fully mixed under heat or without heat. While the amount of the surface-treating agent may be properly selected as required, it is preferably about 0.1 to about 10% by weight based on the amount of the above compound.

The surface-treated compound may be properly subjected to procedures such as washing with water, dehydration, granulation, drying, pulverization, classification, etc., as required, to bring it into the state of a final product.

The compounds of the formulae (1) to (4) of the present invention may be in the form of fine particles having an average secondary particle diameter of about 0.1 to 1 $\mu$m. Further, the above compounds are stable at least up to a processing temperature of about 300° C., and also stable toward ultraviolet or radiation.

Examples of the resin and the rubber used in the present invention include thermoplastic resins such as polyethylene, a copolymer of ethylene with other α-olefin, a copolymer of ethylene with vinyl acetate, ethyl acrylate or methyl acrylate, polypropylene, a copolymer of propylene with other α-olefin, polybutene-1, polystyrene, a copolymer of styrene with acrylonitrile, a copolymer of ethylene with propylene diene rubber or butadiene, vinyl acetate, polyacrylate, polymethacrylate, polyurethane, polyester, polyether, polyamide, polyvinyl chloride, a copolymer of vinyl chloride with vinyl acetate, polyvinylidene chloride, polyphenylene oxide and polycarbonate; thermosetting resins such as a phenol resin, a melamine resin, an epoxy resin, an unsaturated polyester resin and an alkyd resin; and rubbers such as EPDM, SBR, NBR, butyl rubber, isoprene rubber and chlorosulfonated polyethylene.

While the hydraulic cement suitable for use in the present invention shall not be limited specially, examples of the hydraulic cement include portland cement, mixed cement, alumina cement and calcined gypsum. These hydraulic cements may contain known various additives such as a high-performance water reducing agent. Further, the coating composition suitable for use in the present invention shall not be limited specially. Any one of water-based coating compositions can be used.

The present invention will be explained more in detail with reference to Preparation Examples and Examples.

Preparation Example 1

4 liters of a mixed aqueous solution of zinc chloride, magnesium chloride and aluminum chloride ($Zn^{2+}$=0.1 mol/liter, $Mg^{2+}$=0.6 mol/liter and $Al^{3+}$=0.3 mol/liter) and 4 liters of a sodium hydroxide aqueous solution containing 2 mol/liter of sodium hydroxide were added to a reaction vessel having a volume of 2 liters and equipped with an overflow with stirring. The addition rate of the mixed aqueous solution was about 50 ml/minute, and the addition rate of the sodium hydroxide was about 35 ml/minute. During the above additions, pH was maintained at about 9.0 and the temperature was maintained at about 30° C. The obtained reaction mixture slurry was filtrated under reduced pressure, washed with a sodium carbonate aqueous solution containing 0.2 mol/liter of sodium carbonate, further washed with water, dried and pulverized to obtain a dry powder. The so-obtained dry powder had the following chemical structure.

$$Zn_{0.1}Mg_{0.6}Al_{0.3}(OH)_{2.0}(CO_3)_{0.15}nH_2O$$

Preparation Example 2

The same dry powder as obtained in Preparation Example 1 was calcined with a siliconit furnace at 500° C. for 1 hour. The calcined material had the same x-ray diffraction pattern as that of MgO alone. Therefore, it is confirmed that this calcined material was a solid solution in which ZnO and $Al_2O_3$ were dissolved in MgO. The calcined material had the following chemical structure. Table 1 shows the estimation results of the calcined material.

$$Zn_{0.1}Mg_{0.6}Al_{0.3-a}O$$

Preparation Example 3

2 liters of a mixed aqueous solution of copper sulfate, zinc sulfate, magnesium sulfate and aluminum sulfate ($Cu^{2+}$=0.2 mol/liter, $Zn^{2+}$=0.1 mol/liter, $Mg^{2+}$=0.4 mol/liter and $Al^{3+}$=0.3 mol/liter) was added to 2 liters of a sodium hydroxide aqueous solution containing 2 mol/liter of sodium hydroxide with stirring, and the resultant mixture was allowed to react at 30° C. The obtained reaction mixture slurry was filtrated under reduced pressure, washed with a sodium carbonate aqueous solution containing 0.2 mol/liter of sodium carbonate, further washed with water, dried and pulverized. The so-obtained material had the following chemical structure.

$$Cu_{0.2}Zn_{0.1}Mg_{0.4}Al_{0.3}(OH)_{2.0}(CO_3)_{0.15}nH_2O$$

Preparation Example 4

The same dry powder as obtained in Preparation Example 3 was calcined with a siliconit furnace at 500° C. for 1 hour. The calcined material had the same x-ray diffraction pattern as that of MgO alone. Therefore, it is confirmed that this calcined material was a solid solution in which CuO, ZnO and $Al_2O_3$ were dissolved in MgO. The calcined material had the following chemical structure. Table 1 shows the estimation results of the calcined material.

$$Cu_{0.2}Zn_{0.1}Mg_{0.4}Al_{0.3-a}O$$

Preparation Example 5

200 ml of deionized water having 40° C. was charged in a vessel having a volume of 1 liter and made of stainless steel in advance. 500 ml of a Ca(OH) slurry containing 2.0 mol/liter of Ca$(OH)_2$ and 50 ml of a zinc nitrate aqueous solution containing 1.0 mol/liter of zinc nitrate were added to the vessel with stirring. The whole amounts of the above slurry and the above zinc nitrate were added over about 2 minutes. Then, the stirring was continued for further 10 minutes and the mixture was allowed to react. The so-obtained white slurry was dehydrated, washed with water, dried and pulverized. The chemical structure was as follows.

$$Ca_{0.95}Zn_{0.05}(OH)_2$$

Preparation Example 6

2 liters of a mixed aqueous solution of magnesium nitrate and cupric nitrate ($Mg^{2+}$=1.05 mol/liter and $Cu^{2+}$=0.05 mol/liter, 25° C.) was placed in a cylindrical reaction vessel having a volume of 5 liters and made of stainless steel. The whole amount of 2 liters of a Ca$(OH)_2$ aqueous solution (25° C.) containing 1.0 mol/liter of Ca$(OH)_2$ was added with stirring, and the resultant mixture was allowed to react. Then, the reaction mixture was aged under heat at 100° C for 1 hour and filtrated, washed with water, dried and pulverized. The so-obtained material was calcined with a siliconit furnace at 450° C. for 1 hour. The calcined material had the following chemical structure.

$$Mg_{0.95}Cu_{0.05}O$$

Preparation Example 7

2 liters of a mixed aqueous solution of magnesium chloride and zinc chloride ($Mg^{2+}$=2.0 mol/liter and $Zn^{2+}$=0.162 mol/liter) was added to 1.5 liters of a sodium hydroxide aqueous solution containing 3 mol/liter of sodium hydroxide with stirring, and the resultant mixture was allowed to react at 30° C. The obtained reaction mixture slurry was filtrated under reduced pressure, washed with water, dried and pulverized to obtain a pulverized material. The pulverized material was calcined at 900° C. for 1 hour. The calcined material had the following chemical structure.

$$Mg_{0.925}Zn_{0.075}O$$

Preparation Example 8

2 liters of a mixed aqueous solution of copper chloride and calcium chloride ($Cu^{2+}$=0.95 mol/liter and $Ca^{2+}$=0.052 mol/liter) was added to 1.4 liters of a sodium hydroxide aqueous solution containing 3 mol/liter of sodium hydroxide with stirring, and the resultant mixture was allowed to react at 30° C. The obtained reaction mixture slurry was filtrated under reduced pressure, washed with water, dried and pulverized. The dry powder had the following chemical structure.

$$Cu_{0.95}Ca_{0.05}O$$

Example 1

Test of algaeproof in a water tank and results thereof

The dry powders and the calcined materials obtained in Preparation Examples 1 to 8 were granulated with an extruding granulator so as to have a diameter of 3 mm. 8 beakers of 1 liter were prepared. 250 mg of each granule of Preparation Examples 1 to 8 was independently placed into each 1-liter beaker. 1 liter of water was added to each beaker. The contents in the beaker were allowed to stand at ordinary temperatures for 1 year and the state of algal growth was observed.

TABLE 1

|  | PEx. 1 | PEx. 2 | PEx. 3 | PEx. 4 | PEx. 5 | PEx. 6 | PEx. 7 | PEx. 8 | Not added |
|---|---|---|---|---|---|---|---|---|---|
| Estimation | 0 | 0 | 0 | 0 | 0 | 0 | 0 | 0 | 3 |

PEx. = Preparation Example
Note;
estimation standard
0: No growth of algae was found.
1: The growth of algae was slightly found.
2: The growth of algae was found to some extent.
3: The growth of algae was found wholly.

Example 2

Test of algaeproof and fungiproof of hydraulic portland cements and results thereof One of the dry powders and the calcined materials obtained in Preparation Examples 1 to 8 was incorporated into a portland cement such that the amount of one of the dry powders and the calcined materials was 2% by weight based on the portland cement, thereby obtaining a composition. Discard specimens having a diameter of 50 mm and a thickness of 3 mm were obtained from the compositions. The water/cement ratio was 50%. The specimens were aged for 30 days, and then immersed in water for 1 year to observe the states of algal growth and fungi proliferation on surfaces of the specimens. Table 2 shows the results.

TABLE 2

|  | PEx. 1 | PEx. 2 | PEx. 3 | PEx. 4 | PEx. 5 | PEx. 6 | PEx. 7 | PEx. 8 |
|---|---|---|---|---|---|---|---|---|
| Algaeproof | 0 | 0 | 0 | 0 | 1 | 0 | 0 | 0 |
| Fungiproof | 0 | 0 | 0 | 0 | 0 | 0 | 0 | 0 |

PEx. = Preparation Example
Note;
estimation standard
0: No growth of algae was found.
1: The growth of algae was slightly found.
2: The growth of algae was found to some extent.
3: The growth of algae was found on all surfaces.

In the above test, when a specimen contained no dry powders or calcined material, the growth of algae was found on all the surfaces of the specimen.

Example 3

Proofness of alga cells-growth when selenastrum capricorutum cells were incorporated Three beakers were prepared. 1 liter of distilled water was independently poured to each beaker, and selenastrum capricorutum cells were added to each beaker so as to have a concentration of $2 \times 10^4$ cells/ml. $Mg_3ZnAl_2(OH)_{12}CO_3 \cdot 3H_2O$ was added to one of the beakers so as to have a concentration of 56 mg/liter, and $Mg_3ZnAl_2(OH)_{12}CO_3 \cdot 3H_2O$ was added to another beaker of the above beakers so as to have a concentration of 100 mg/liter. The other beaker contained no hydroxide solid solution and it was used as a referential example. The contents of the beakers were investigated for the growth of algae cells. Table 3 shows the results.

TALE 3

| Time (hours) | Referential Example | 56 mg/liter | 100 mg/liter |
|---|---|---|---|
| 0 | 2.00 | 2.00 | 2.00 |
| 24 | 6.46 | 1.00 | 1.00 |
| 48 | 31.60 | 1.00 | 1.00 |
| 72 | 127.10 | 15.00 | 1.00 |

Unit = $\times 10^4$ cells/milliliter

Industrial Utilities

According to the present invention, there is provided an inhibitor which exhibits excellent effects of preventing the growth of algae and the proliferation of microorganisms in water-use facilities. According to the present invention, further, there is provided an organic or inorganic material containing the above inhibitor.

What is claimed is:

1. An antialgal method which comprises applying at least one solid solution selected from the group consisting of the compounds of the formulae (1) to (4), the compounds of the formulae (1) to (4) being a hydroxide solid solution of the formula (1), $$[(M_1^{2+})_y(M_2^{2+})_{1-y}]_{1-x}M^{3+}_x(OH)_2(A^{n-})_{y/n} \cdot mH_2O \quad (1)$$

wherein y is a number in the range of $0 \leq y \leq 1$, x is a number in the range of $0 < x \leq 0.5$, m is a number in the range of $0 \leq m \leq 2$, $M_1^{2+}$ is $Zn^{2+}$ and/or $Cu^{2+}$, $M_{2+}^{2+}$ is $Mg^{2+}$ and/or $Ca^{2+}$, $M^{3+}$ is at least one trivalent metal, and $A^{n-}$ is an anion of n valence, an oxide solid solution of the formula (2), $$[(M_1^{2+})_y(M_2^{2+})_{1-y}]_{1-x}M^{3+}_{x-a}O \quad (2)$$

wherein y is a number in the range of $0 \leq y \leq 1$, x is a number in the range of $0 < x \leq 0.5$, x–a means that the number of $M^{3+}$ is decreased by a due to a lattice defect, and $M_1^{2+}$ and $M_2^{2+}$ have the same meanings as those defined in the formula (1), a hydroxide solid solution of the formula (3), $$(M_1^{2+})_x(M_2^{2+})_{1-x}(OH)_2 \quad (3)$$

wherein x is a number of $0.001 \leq x < 0.9$, and $M_1^{2+}$ and $M_2^{2+}$ have the same meanings as those defined in the formula (1), and an oxide solid solution of the formula (4), $$(M_1^{2+})_x(M_2^{2+})_{1-x}O$$

wherein x is a number of $0.001 \leq x < 0.9$, and $M_1^{2+}$ and $M_2^{2+}$ have the same meanings as those defined in the formula (1), to an area in which algal growth is to be inhibited.

2. The antialgal method according to claim 1 wherein the solid solution is surface-treated with at least one surface-treating agent selected from the group consisting of a higher fatty acid, an alkaline metal salt of higher fatty acid, an alkaline-earth metal salt of higher fatty acid, phosphates, a silane-containing coupling agent, a titanate-containing coupling agent, an aluminum-containing coupling agent, and esters of a polyalcohol and a fatty acid.

3. The antialgal method according to claim 1, which contains 100 parts by weight of an organic or inorganic material which organic or inorganic material contains 0.001 to 50 parts by weight of the active component.

4. The antialgal method according to claim 3 wherein the organic or inorganic materials is at least one material selected from the group consisting of a resin, a rubber, a hydraulic cement composition and a coating composition.

* * * * *